United States Patent [19]

Kolde

[11] Patent Number: 4,784,944
[45] Date of Patent: Nov. 15, 1988

[54] PROTHROMBIN TIME DETERMINING REAGENT AND METHODS OF USING AND PREPARING THE SAME

[75] Inventor: Hans-Jürgen Kolde, Marburg, Fed. Rep. of Germany

[73] Assignee: Behringwerke Aktiengesellschaft, Fed. Rep. of Germany

[21] Appl. No.: 720,348

[22] Filed: Apr. 5, 1985

[30] Foreign Application Priority Data

Apr. 9, 1984 [DE] Fed. Rep. of Germany ....... 3413311

[51] Int. Cl.$^4$ .......................... C12Q 1/56; G01N 33/86
[52] U.S. Cl. .......................................... 435/13; 436/69
[58] Field of Search .......................... 436/69; 435/13; 260/112.5 L; 530/330, 331, 332

[56] References Cited

U.S. PATENT DOCUMENTS

| | | | |
|---|---|---|---|
| 3,520,659 | 7/1970 | Steinberg et al. | 436/69 |
| 3,527,569 | 9/1970 | Mass | 436/69 X |
| 3,983,004 | 9/1976 | Trobisch et al. | 436/69 X |
| 4,070,245 | 1/1978 | Svendsen | 435/13 |
| 4,169,015 | 9/1979 | Ekerstam et al. | 435/13 |
| 4,289,498 | 9/1981 | Baughman et al. | 436/69 X |
| 4,409,334 | 10/1983 | Lill et al. | 436/69 X |
| 4,458,015 | 7/1984 | Jering et al. | 435/13 |
| 4,508,644 | 4/1985 | Heber et al. | 260/112.5 L |

FOREIGN PATENT DOCUMENTS 0003474 8/1979 European Pat. Off.
917012 1/1963 United Kingdom.

OTHER PUBLICATIONS

Paulssen et al, Clin. Chem. Acta, vol. 92, pp. 465–468, 1979.
Becker et al., Clin. Chem., vol. 30, No. 4, pp. 524–528, 4/7/84.
van Wijk et al., Clin. Chem., vol. 26, No. 7, pp. 885–890, 1980.
Talstad, Chemical Abstracts, vol. 93, Abstract No. 93:142534w, 1980.

Primary Examiner—Barry S. Richman
Assistant Examiner—Robert J. Hill, Jr.
Attorney, Agent, or Firm—Finnegan, Henderson, Farabow, Garrett & Dunner

[57] ABSTRACT

A reagent for the photometric determination of the prothrombin time is described. The reagent contains a thromboplastin and a chromogenic substrate for thrombin, wherein this substrate is cleaved by the thromboplastin at only a low reaction rate. This reagent can be used for the determination of coagulation factors with the use of deficient plasma. Also disclosed is a method of preparing the reagent.

13 Claims, No Drawings

PROTHROMBIN TIME DETERMINING REAGENT AND METHODS OF USING AND PREPARING THE SAME

The invention relates to a reagent for the determination of the prothrombin time using a chromogenic substrate for thrombin.

The determination of the prothrombin time (PT) is one of the most frequently performed coagulation tests. Due to the use of the PT to monitor oral anticoagulant therapy with coumarin derivatives, this test has become of increasing importance, especially due to the fact that the success of therapy is crucially dependent on monitoring for maintenance of the therapeutic range.

In the determination of the PT, the plasma or blood sample is activated with a tissue thromboplastin from animal or human tissue. The tissue thromboplastin activates the factor VII in the exogenous coagulation system, and this factor liberates, via activation of factor X, thrombin from prothrombin. In conservative coagulation analyses, the thrombin is then determined by measurement of the coagulation time using the natural substrate fibrinogen. It is of crucial importance that the tissue thromboplastin has high sensitivity to all vitamin K-dependent coagulation factors of the exogenous coagulation pathway, II, VII and X, since these are decreased by the coumarin therapy. The British comparative thromboplastin, which is accepted as international standard, detects these factors with high sensitivity.

So-called II, VII and X reagents are also used for monitoring anticoagulant therapy. Factor V and fibrinogen are added to these thromboplastin reagents in order to rule out variations in the content of these factors. By this means, it becomes possible for plasma or blood samples to be stored for a certain time before being investigated, since factor V, which has a crucial effect on the PT, rapidly loses activity.

Since factor VII has the shortest biological halflife, it responds most rapidly to therapy with coumarin derivatives. For this reason, factor VII-sensitive thromboplastins are regarded as particularly suitable also for monitoring the initial phase of anticoagulation of a patient. Checks on factor X are likewise indicated in the initial phase (Aiach, M. et al., 1982, Thromb. Res. 47, 69–71), so that factor X-sensitivity is also desirable.

It has been possible for some time, due to the development of low molecular weight chromogenic peptide substrates for the activated factors of the coagulation cascade, to replace the classic coagulation substrate fibrinogen. Thus, nowadays there are relatively specific substrates for the vitamin K-dependent factors X and II. Sensitive methods for the determination of factors X, VII and II in plasma have been developed, and it has been possible to achieve relatively favorable correlations between the PT determination and the determinations of the individual factors. The disadvantage of all these determinations of the individual factors is that they detect only one of the vitamin K-dependent factors and thus do not reflect the pathophysiological situation of the patient in whom there is a decrease of all three factors. In particular, the critical factor VII cannot even nowadays be measured directly with a specific chromogenic substrate, but can only be measured via factor X.

A method has been described, in European Pat. No. A-0,014,039, in which the PT is determined using a chromogenic substrate. However, in order to achieve reasonable measurement times, a so-called serum reagent is needed, and this is obtained from recalcified plasma by thromboplastin activation. Experience has shown that the processing of the serum which is described does not guarantee the complete removal of all factors, in particular those of the exogenous coagulation pathway. Thus, a thromboplastin which is used in combination with a serum which has been prepared in the manner described cannot have a high factor-sensitivity, especially not when, as proposed in the patent, thrombin is added directly to the reagent.

Another method and reagent for the measurement of the prothrombin time using a chromogenic substrate have been presented in German Pat. No. A-3,113,350. In order to obtain a sufficiently stable reagent, it is necessary to use a specially prepared thromboplastin. This is because the thrombin substrate used in this application is subject to non-specific hydrolysis by proteases which are already present in the thromboplastin. However, these proteases were essentially removed during the modified method of preparation of the thromboplastin, so that the reagent has considerably improved stability. It is desirable, however, for reasons of comparability of photometric with coagulometric methods for the determination of the prothrombin time, for the two types of reagent to be prepared from the same thromboplastin. In addition, it is then possible to obtain a reagent for both photometry and coagulometry from one processing of thromboplastin.

Surprisingly, a reagent of this type can be prepared using conventional thromboplastins if a chromogenic substrate having high specificity for thrombin is used, for example H-D-Phe-Pro-Arg-ANBA-isopropylamide or other ANBA derivatives, such as ANBA-glycine ethyl ester or ANBA-neopentylamide. The invention relates to a reagent of this type.

Table 1 shows the results of hydrolysis of chromogenic substrates for various proteases by thromboplastin preparations of the state of the art. By measurement of the extinction at 405 nm, it is seen that thrombin substrates having the structure H-D-Phe-Pro-Arg-ANBA-R, Tos-Gly-Pro-Arg-ANBA-R or Boc-Gly-Pro-Arg-ANBA-R are hydrolyzed to only an inconsiderable extent by the thromboplastins, while a rapid consumption of the substrate is recorded for most of the other substrates including the substrate for thrombin used in German Pat. No. 3,113,350 A1, Tos-Gly-Pro-Arg-pNA. Thus all the thromboplastins exhibit a high proteolytic activity. This means in practice that this type of reagent with a substrate such as Tos-Gly-Pro-Arg-pNA is stable for only a very short time, since there is a rapid decrease in the amount of substrate which is used. In contrast, a reagent with, for example, H-D-Phe-Pro-Arg-ANBA-isopropylamide is stable for a considerably longer time and its stability is limited by the stability of the thromboplastin and not by the hydrolysis of the substrate.

Thus the properties of this type of reagent are very comparable with those of a coagulation reagent using the same thromboplastin.

Hence the invention relates to a reagent for the photometric determination of the prothrombin time, containing, at the least, a thromboplastin having proteolytic activity and a chromogenic substrate for thrombin, which comprises the chromogenic substrate for thrombin being converted by the thromboplastin having proteolytic activity, in aqueous suspension in the presence of calcium ions, to the extent of less than 0.00125 times the initial concentration per hour at 37° C.

The thromboplastin is preferably obtained from human placenta.

A chromogenic substrate which is preferably used has the structure Tos-Gly-Pro-Arg-ANBA-R or H-D-Phe-Pro-Arg-ANBA-R, where R is $NH-C_nH_{2n+1}$, with n=1 to 7, NH-benzyl or the residue of an amino acid, or its alkyl ester, which is bonded via the α-amino group.

The reagent described can contain calcium ions at a concentration of 0.5 to 10 mmol/l, preferably 5 mmol/l.

It can additionally contain a buffer solution such as tris, HEPES, glycylglycine, EPPS and imidazole, preferably HEPES, at a concentration of 0.005 to 0.1 mol/l, preferably 0.025 mol/l, with a pH range from 7 to 8.5, preferably 7.6.

It is also possible to add neutral salts, preferably sodium chloride, at a concentration of 0.01 to 0.2 mol/l, preferably 0.05 mol/l.

This type of reagent can also contain a heparin inhibitor such as protamine salts or polybrene ®, particularly Polybrene ®, in a concentration of 0.01 to 0.5 mg/l, preferably 0.25 mg/l. Polybrene ® is the trademark for Hexadimethrine bromide (1,5-dimethyl-1,5-diazaundecamethylen-polymethobromide).

It is also possible to add human or animal factor V to the reagent.

With the use of a plasma deficient in factors II, VII, X and V, the reagent descrlbbed can be used for the determination of factors II, VII, X and V, or with the use of a plasma deficient in factors II, VII and X, it can be used for the determination of factors II, VII and X.

The abbreviations used are explained below:
ANBA: 5-amino-24-nitrobenzoic acid
Phe: phenylalanine
Pro: proline
Arg: arginine
Tos: toluenesulfonyl
Gly: glycine
Tris: trishydroxymethylaminomethane
HEPES: N-(2-hydroxyethyl)piperazine-N'-2-ethanesulfonic acid
EPPS: 4-(2-hydroxyethyl)-1-piperazinepropanesulfonic acid
Leu: leucine
pNA: para-nitroaniline
Suc: succinyl
Ala: alanine.

TABLE 1

Hydrolysis of various chromogenic substrates by thromboplastins of the state of the art

| Chromogenic substrate | Thromboplastin | | | | | | |
|---|---|---|---|---|---|---|---|
| | A | B | C | D | E | F | G |
| D-Phe—Pro—Arg—ANBA-isopropylamide | 0,006 | 0,016 | 0,010 | 0,013 | 0,011 | 0 | 0 |
| D-Phe—Pro—Arg—ANBA-Valine methyl ester | 0,003 | 0,031 | 0,008 | 0,020 | 0 | 0 | 0,002 |
| D-Phe—Pro—Arg—ANBA-neopentylamide | 0,003 | 0,009 | 0,011 | 0,007 | 0,014 | 0,003 | 0,002 |
| D-Phe—Pro—Arg—ANBA-Glycine ethyl ester | 0,007 | 0,009 | 0,015 | 0,019 | 0,008 | 0,011 | 0,003 |
| D-Phe—Pro—Arg—ANBA-n-Butyl-amide | 0,021 | 0,023 | 0,019 | 0,013 | 0,030 | 0,023 | 0,012 |
| Tos—Gly—Pro—Arg—ANBA-isopropylamide | 0,035 | 0,039 | 0,030 | 0,023 | 0,041 | 0,029 | 0,018 |
| Tos—Gly—Pro—Arg—ANBA-Glycine ethyl ester | 0,029 | 0,034 | 0,028 | 0,026 | 0,037 | 0,023 | 0,029 |
| Tos—Gly—Pro—Arg—pNA | 0,190 | 0,143 | 0,115 | 0,137 | 0,123 | 0,116 | 0,149 |
| Leu—pNA | 0,974 | 0,681 | 0,721 | 0,593 | 0,871 | 0,536 | 1,124 |
| Suc—(Ala)₃-pNA | 0,211 | 0,324 | 0,248 | 0,411 | 0,178 | 0,310 | 0,202 |
| N—α-Benzoyl-L-Lysine-pNA | 0,319 | 0,525 | 0,433 | 0,402 | 0,372 | 0,198 | 0,503 |

Difference in extinction after 92 hours at room temperature of a reagent prepared according to Example 1. The substrate concentration was 50 μmol/l, and the thromboplastins were dissolved in accordance with the statements of the manufacturer and added at a concentration of 5%.

The examples which follow are intended to illustrate the invention further:

EXAMPLE 1

Preparation of a reagent for the determination of the prothrombin time using a chromogenic substrate 4 to 20 ml of human thromboplastin were added to 70 ml of an aqueous solution containing 5.844 g of NaCl, 1.47 g of CaCl₂, 11.92 g of HEPES, 250 μg of polybrene ® and 67.1 mg of H-D-Phe-Pro-Arg-ANBA-isopropylamide HCl in one liter, pH 7.6, and the mixture was freeze-dried.

Depending on the amount and activity of the thromboplastin added, after reconstitution with 200 ml of water the time obtained for a change of 0.1 in extinction at 405 nm was from 20 to 40 sec with a normal plasma.

EXAMPLE 2

1. Reference curve

Reagent mixture as in Example 1. Serial dilutions of plasma with physiological sodium chloride solution were made up and the prothrombin time was measured by photometry.

500 μl of reagent were added to 50 μl of plasma or diluted plasma in a prewarmed plastic cell, and the extinction at 405 nm was recorded as a function of time. The time at which an increase of 0.1 in extinction is reached is determined from the graph. This time is plotted against the reciprocal of the plasma concentration. A straight line between 100 and 5% of normal is obtained, similar to the coagulation method. The normal figure for the undiluted plasma is 29.4 seconds. The times are considerably longer for pathological plasmas.

2. Factor sensitivity

The sensitivity of a reagent according to Example 1 for factors II, VII, X and V is shown in Table 2. Plasma was diluted with the appropriately deficient plasmas and analyzed as in 1.

TABLE 2

| | Prothrombin ratio Content of the factor as a % of normal | | |
|---|---|---|---|
| Factor | 100 | 25 | 10 |
| X | 1 | 1.35 | 1.75 |
| VII | 1 | 1.2 | 5.8 |
| II | 1 | 1.2 | 1.56 |
| V | 1 | 1.75 | 3.65 |

It can be seen from Table 2 that the reagent responds sensitively to a decrease in the factors listed.

I claim:

1. A reagent for the photometric determination of prothrombin time, comprising a freeze-dried mixture of a thromboplastin having proteolytic activity, hexadimethrine bromide and an ANBA chromogenic substrate for thrombin, wherein the substrate is such that it is converted by the thromboplastin, in aqueous suspension in the presence of calcium ions, to the extent of less than 0.00125 times its initial concentration per hour at 37° C.

2. The reagent as claimed in claim 1, wherein the thromboplastin is obtained from human placenta.

3. The reagent as claimed in claim 1, wherein the chromogenic substrate has the structure H-D-Phe-Pro-Arg-ANBA-R or Tos-Gly-Pro-Arg-ANBA-R, where R is $NH-C_nH_{2n+1}$, with n=1 to 7, NH-benzyl or a residue of an amino acid, or its alkyl ester, which is bonded via its α-amino group.

4. The reagent as claimed in claim 1, wherein the freeze-dried mixture further comprises a material which yields calcium ions when added to water.

5. The reagent as claimed in claim 1, wherein the freeze-dried mixture further comprises human or animal factor V.

6. The reagent as claimed in claim 1, wherein the freeze-dried mixture further comprises a buffer selected from the group consisting of tris, HEPES, glyclglycine, EPPS, and imidazole.

7. The reagent as claimed in claim 6, wherein said buffer is HEPES.

8. The reagent as claimed in claim 1, wherein the freeze-dried mixture further comprises a neutral salt.

9. The reagent as claimed in claim 8, wherein said neutral salt is sodium chloride.

10. A process for preparing a reagent containing a thromboplastin having proteolytic activity and an ANBA chromogenic substrate for thrombin for photometric determination of prothrombin time, comprising adding an ANBA chromogenic substrate for thrombin and a thromboplastin having proteolytic activity to a buffer solution having a pH in the range of 7-8.5 to form a mixture and freeze drying the mixture, wherein the ANBA chromogenic substrate is such that it is converted by the thromboplastin, in aqueous suspension in the presence of calcium ions, to the extent of less than 0.00125 times its initial concentration per hour at 37° C.

11. The process of claim 10 wherein a calcium salt is also added to the buffer solution, the calcium salt being soluble in the buffer and present in the mixture in a concentration of 0.5-10 mmol/l.

12. A method for the photometric determination of prothrombin time in plasma, which comprises providing a material which yields calcium ions when added to water, providing a freeze-dried mixture of a thromboplastin having proteolytic activity and an ANBA chromogenic stubstrate for thrombin which is converted by the thromboplastin, in the presence of calcium ions, to the extent of less than 0.00125 times its intial concentration per hour at 37 C., adding the material and the freeze-dried mixture to water to form a solution which contains calcium ions at a concentration of 0.5-10 mmol/l, diluting a plasma sample with the solution to form a plasma mixture, and determining the prothrombin time in the plasma sample by determining the time in which a specified extinction increase is obtained in the plasma mixture.

13. The method as claimed in claim 12, wherein the plasma sample is diluted in a plasma deficient in one of the clotting factors II, V, VII or X prior to being diluted with the solution.

* * * * *